United States Patent [19]
Ripley et al.

[11] Patent Number: 5,736,165
[45] Date of Patent: Apr. 7, 1998

[54] IN-THE-EYE USE OF CHLORINE DIOXIDE-CONTAINING COMPOSITIONS

[75] Inventors: Paul S. Ripley, Irvine; Anthony J. Dziabo, Lake Forest; Claude B. Anger, Long Beach, all of Calif.

[73] Assignee: Allergan, Waco, Tex.

[21] Appl. No.: 277,718

[22] Filed: Jul. 20, 1994

Related U.S. Application Data

[63] Continuation-in-part of Ser. No. 66,746, May 25, 1993, abandoned.

[51] Int. Cl.$^6$ .......................... A61K 33/20; A61K 33/40; A01N 59/00
[52] U.S. Cl. .......................... 424/661; 424/662; 424/663; 424/664; 424/665; 424/613; 424/615; 514/912; 514/914; 422/37
[58] Field of Search .......................... 424/661, 662, 424/663, 664, 665, 613, 615; 422/37; 514/912, 914

[56] References Cited

U.S. PATENT DOCUMENTS

| | | | |
|---|---|---|---|
| Re. 23,218 | 4/1950 | Levy | 162/87 |
| Re. 32,672 | 5/1988 | Huth et al. | 435/264 |
| 2,436,134 | 2/1948 | Aston | 423/477 |
| 2,477,631 | 8/1949 | Levy et al. | 162/87 |
| 3,123,521 | 3/1964 | Wentworth | 424/615 |
| 3,278,447 | 10/1966 | McNicholas | 252/186.21 |
| 3,386,915 | 6/1968 | Rutschi | 210/754 |
| 3,563,702 | 2/1971 | Partridge | 423/478 |
| 3,585,147 | 6/1971 | Gordon | 252/187.21 |
| 3,591,515 | 7/1971 | Lovely | 252/186.22 |
| 3,622,479 | 11/1971 | Schneider | 210/748 |
| 3,763,006 | 10/1973 | Callerame | 205/556 |
| 3,819,828 | 6/1974 | McCoy | 424/70.4 |
| 3,910,296 | 10/1975 | Karageozian et al. | 134/2 |
| 3,912,451 | 10/1975 | Galia, Jr. | 422/30 |
| 4,011,941 | 3/1977 | Parsons | 206/5.1 |
| 4,084,747 | 4/1978 | Alliger | 422/20 |
| 4,104,190 | 8/1978 | Hartshorn | 252/187.21 |
| 4,123,376 | 10/1978 | Gray | 510/307 |
| 4,146,496 | 3/1979 | Gray | 8/111 |
| 4,202,740 | 5/1980 | Stoner et al. | 205/701 |
| 4,236,992 | 12/1980 | Themy | 204/278 |
| 4,361,471 | 11/1982 | Kosarek | 210/748 |
| 4,386,160 | 5/1983 | Branner-Jorgensen | 435/221 |
| 4,456,510 | 6/1984 | Murakami | 205/556 |
| 4,459,217 | 7/1984 | Bogie | 510/117 |
| 4,496,452 | 1/1985 | Bianchi | 204/266 |
| 4,499,077 | 2/1985 | Stockel et al. | 424/661 |
| 4,557,925 | 12/1985 | Lindahl et al. | 424/482 |
| 4,568,517 | 2/1986 | Kaspar et al. | 422/30 |
| 4,614,549 | 9/1986 | Ogunbuyi et al. | 134/19 |
| 4,618,444 | 10/1986 | Hudson et al. | 8/111 |
| 4,654,208 | 3/1987 | Stockel et al. | 424/78.08 |
| 4,689,169 | 8/1987 | Mason et al. | 252/186.24 |
| 4,689,215 | 8/1987 | Ratcliff | 424/53 |
| 4,690,773 | 9/1987 | Ogunsbuyi et al. | 435/264 |
| 4,731,192 | 3/1988 | Kenjo et al. | 510/113 |
| 4,767,559 | 8/1988 | Kruse et al. | 510/114 |
| 4,786,492 | 11/1988 | Ratcliff | 424/53 |
| 4,788,053 | 11/1988 | Ratcliff | 424/53 |
| 4,792,442 | 12/1988 | Ratcliff | 424/53 |
| 4,837,009 | 6/1989 | Ratcliff | 424/53 |
| 4,855,135 | 8/1989 | Ratcliff | 424/961 |
| 4,861,514 | 8/1989 | Hutchings | 510/102 |
| 4,971,760 | 11/1990 | Rubinstein | 422/37 |
| 4,986,990 | 1/1991 | Davidson et al. | 424/665 |
| 4,997,626 | 3/1991 | Dziabo et al. | 422/37 |
| 5,077,258 | 12/1991 | Phillips | 502/321 |
| 5,078,908 | 1/1992 | Ripley et al. | 252/187.21 |
| 5,129,999 | 7/1992 | Holland et al. | 205/701 |
| 5,135,623 | 8/1992 | Dziabo et al. | 205/701 |
| 5,152,912 | 10/1992 | Dziabo et al. | 510/112 |
| 5,197,636 | 3/1993 | Mitchell et al. | 222/190 |
| 5,279,673 | 1/1994 | Dziabo et al. | 134/26 |
| 5,424,078 | 6/1995 | Dziabo et al. | 424/661 |

FOREIGN PATENT DOCUMENTS

| | | |
|---|---|---|
| 520668 | 12/1987 | Australia. |
| 1156420 | 11/1983 | Canada. |
| 0082798 | 6/1983 | European Pat. Off.. |
| 0147100 | 7/1985 | European Pat. Off.. |
| 0168253 | 1/1986 | European Pat. Off.. |
| 0196075 | 1/1986 | European Pat. Off.. |
| 0199385 | 10/1986 | European Pat. Off.. |
| 0209071 | 1/1987 | European Pat. Off.. |
| 0240315 | 10/1987 | European Pat. Off.. |
| 0279401 | 2/1988 | European Pat. Off.. |
| 0255041A1 | 5/1988 | European Pat. Off.. |
| 0278224 | 8/1988 | European Pat. Off.. |
| 0384666 | 8/1990 | European Pat. Off.. |
| 0426489 | 5/1991 | European Pat. Off.. |
| 3626082A1 | 11/1988 | Germany. |
| 1269677 | 4/1982 | United Kingdom. |
| 2094992 | 9/1982 | United Kingdom. |
| 2139260 | 11/1984 | United Kingdom. |
| 2173017 | 10/1986 | United Kingdom. |
| 2187748 | 9/1987 | United Kingdom. |
| 2151039 | 7/1988 | United Kingdom. |
| WO 8704107 | 9/1985 | WIPO. |
| WO 8605695 | 10/1986 | WIPO. |
| 8903179 | 4/1989 | WIPO. |
| WO 8911878 | 12/1989 | WIPO. |
| WO9006126 | 6/1990 | WIPO. |

OTHER PUBLICATIONS

Siu et al, "Effect of Succinylation on the Protein Quality and Urinary Excretion of Bound and Free Amino Acids", J. Agric. Food Chem 1982, 30, 1179–1183.

Communications to the Editor, "Stabilization of Microbial Proteases against Autolysis Using Acylation with Dicarboxylic Acid Anhydrides", Biotechnology and Bioengineering, vol. XXIV, pp. 483–486(1982).

(List continued on next page.)

*Primary Examiner*—John Pak
*Attorney, Agent, or Firm*—Frank J. Uxa

[57] ABSTRACT

Disclosed are in-the-eye uses of chlorine dioxide-containing compositions as effective ophthalmic antiseptics and as effective ophthalmic surgical irrigants. Surprisingly low concentrations of chlorine dioxide are effective in such applications. In addition, the presently useful compositions are ophthalmically acceptable.

22 Claims, No Drawings

OTHER PUBLICATIONS

Kennedy et al., "The Oxidation of Organic Substances by Potassium Peroxymonosulfate", J. Organic Chemistry 25:1901–1906 (1960).

Polymers Letters Edition, "A Study of Ozone Attack On Elastomer Surfaces BY Attenuated Total Reflectance Spectroscopy", vol. 12, pp. 281–286 (1974).

Manivannan et al, "Peroxo Salts As Initiators Of Vinyl Polymerization–II", Eur, Polym, J. vol. 23, No. 4, pp. 311–313 (1987).

Evans et al, Phase Transfer Controlled Selective Oxidation Of Diarylsulfides to Diarylsulfoxides Using Potassium Hydrogen Persulfate, Synthetic Communications, 16(10), 1207–1216 (1986).

Bloch et al, Epoxidation of Alkenes with Potassium Hydrogen Persulfate J. Org. Chem. 1985, 50:1544–1545.

Ball, Jr. et al., "Acylation of Egg White Proteins with Acetic Anhydride and Succinic Anhydride", Poultry Science 1982 61:1041–1046.

W. Masschelein, "Preparation of Pure Chlorine Dioxide", vol. 6, No. 2, Jun. 1967.

I. Klotz, "Succinylation", Methods in Enzymology, vol. XI, Enzyme Structure, 1967, 576–580.

De Poorter et al, "Oxone As Oxygen Donor in The Catalytic Hydroxylation of Saturated Hydrocarbons", Tetrahedron Letters, vol. 26, No. 32, pp. 4459–4462 (1985).

Trost et al, "Chemoselective Oxidation of Sulfides to Sulfones with Potassium Hydrogen Persulfate", Tetrahedron Letters, vol. 22, No. 14, pp. 1287–1290 (1981).

ns5,736,165

IN-THE-EYE USE OF CHLORINE DIOXIDE-CONTAINING COMPOSITIONS

RELATED APPLICATIONS

This application is a continuation-in-part of application Ser. No. 08/066,746, filed May 25, 1993, now abandoned, which application is incorporated in its entirety herein by reference.

BACKGROUND OF THE INVENTION

The present invention relates to new uses of chlorine dioxide-containing compositions. More particularly, the invention relates to uses of compositions including effective amounts of chlorine dioxide in the eye to obtain surprising benefits without detrimentally affecting the eye.

The use of chlorine dioxide dissolved in an aqueous liquid medium to disinfect contact lenses has previously been suggested. See, for example, the following U.S. Patents: U.S. Pat. Nos. 4,997,626; 5,279,673; 5,078,908; and 5,129,999, each of which is incorporated in its entirety herein by reference. After disinfection, the contact lenses are removed from the liquid medium and placed in the eye for safe and comfortable wear. Alternately, the disinfected contact lens can be rinsed free of residual chlorine dioxide-containing liquid medium and, then, placed in the eye for safe and comfortable wear. Thus, although small, residual amounts chlorine dioxide have been found to be relatively innocuous in the eye, no suggestion has been made regarding using effective amounts of chlorine dioxide in the eye.

Various compositions have been suggested for use in the eye to produce effects while in the eye. For example, ophthalmic antiseptics have been used to treat a variety of ocular infections, for example, bacterial conjunctivitis and the like. One problem that has existed with regard to prior ophthalmic antiseptic compositions is that the effective ingredients tend to lose potency or effectiveness over a period of time. Thus, such compositions have a relatively short shelf life before becoming ineffective. Higher concentrations of the effective ingredient or ingredients can be included in such compositions to compensate for the gradual loss of potency. However, such higher concentrations of active ingredients tend to have adverse effects on the eye being treated. Clearly it would be advantageous to provide ophthalmic antiseptic compositions which have relatively long shelf lives and/or include active ingredients which are effective at concentrations which do not adversely affect the eye.

Another in-the-eye use of compositions has been as surgical irrigants to effectively irrigate an ocular surgical area. Because the ocular surgical area is being subjected to surgical trauma, it is important that the irrigant be effective without causing any additional harm to the eye. Prior art compositions have, for the most part, been focused on providing a sterile liquid, such as a buffered saline solution, as an irrigant. Although sterile buffered saline does not contaminate the ocular surgical area, it is relatively ineffective in removing or reducing microbial contamination that may be present from other sources. It would be advantageous to provide ocular surgical irrigants which are not only effective as irrigants but also are antimicrobially effective in the ocular surgical area.

SUMMARY OF THE INVENTION

New uses for chlorine dioxide-containing compositions in the eye have been discovered. Surprisingly, it has been found that relatively low concentrations of chlorine dioxide are sufficient to be effective ophthalmic antiseptics and to be antimicrobially active in ocular surgical areas. Compositions, which include such effective amounts of chlorine dioxide, have been found to be ophthalmically acceptable for in-the-eye use. The present invention is easy and straightforward to practice. For example, the invention can be practiced using techniques used in employing prior art ophthalmic antiseptics and ocular surgical irrigants. Little or no additional cost is involved in practicing the present invention relative to using conventional ophthalmic antiseptics and ocular surgical irrigants. The chlorine dioxide-containing compositions useful in the present methods can be formed from stable precursor compositions very shortly (directly) prior to use. Such precursor compositions have relatively long shelf lives, and produce chlorine dioxide-containing compositions having reliable and reproducible chlorine dioxide concentrations which are effective as ophthalmic antiseptics and ocular surgical irrigants, and are ophthalmically acceptable.

As used herein, the term "ophthalmically acceptable" refers to any material or combination of materials which, in the concentrations employed, has no undue detrimental effect on the eye or the ocular tissue with which it comes in contact.

In one broad aspect of the present invention, methods for caring for a mammalian eye are provided. These caring methods comprise administering to a mammalian eye, preferably a human eye, an effective amount of a composition, preferably in the form of an aqueous liquid medium, which includes chlorine dioxide in an amount effective as an antiseptic in the eye. The amount of chlorine dioxide is less than about 50 or about 25 parts per million (ppm) by weight of the composition. Such administering is particularly effective where the eye has a microbial infection, such as bacterial conjunctivitis and/or other microbial infection, since such administering is effective in treating, preferably reducing or even eliminating, the microbial infection. The presently useful compositions preferably have a pH in the range of about 6 to about 10 and/or are substantially isotonic.

In another broad aspect of the present invention, methods of irrigating ocular tissue during ophthalmic surgery are provided. Such irrigating methods comprise administering to an area of a mammalian eye, preferably a human eye, undergoing a surgical procedure an amount of a composition effective to irrigate the area. This composition is ophthalmically acceptable and includes chlorine dioxide in an antimicrobially effective amount. Preferably, the administering is effective in disinfecting the ocular surgical area, that is the area of the eye coming in contact with the irrigating composition. Preferably the presently useful compositions include chlorine dioxide in an effective disinfecting amount. The presently useful irrigating compositions are preferably present in the form of an aqueous liquid medium, and more preferably have a pH in the range of about 6 to about 10 and/or are substantially isotonic.

These and other aspects and advantages of the present invention will become apparent hereinafter, particularly when considered in conjunction with the examples and claims.

DETAILED DESCRIPTION OF THE INVENTION

The present invention is directed to new in-the-eye uses of compositions including effective amounts of chlorine dioxide. Such compositions have been found to be effective as ophthalmic antiseptics or ophthalmic surgical irrigants while having no adverse effects on the ocular tissue coming into contact with the compositions.

Methods for caring for a mammalian, preferably human, eye are provided employing a chlorine dioxide-containing composition as an effective antiseptic. As used herein, the term "antiseptic" refers to a material or combination of materials which is effective, in the concentration employed, to kill microorganisms, for example, bacteria, with which it comes in contact. Specifically with regard to an ophthalmic antiseptic, such material or combination of materials is effective to at least reduce, or even eliminate, an existing microbial, for example, bacterial, infection in an eye with which it comes in contact and/or to prevent microbial infections in an eye with which it comes in contact.

In general, the present eye caring methods comprise administering to a mammalian eye an effective amount of a composition which includes chlorine dioxide in an amount effective as an antiseptic in the eye. The amount of chlorine dioxide is less than about 50 or less than about 25 parts per million (ppm) by weight of the composition. Such administering is particularly effective where the eye is susceptible to or has a microbial infection, such as bacterial conjunctivitis, since such administering is particularly effective in preventing or treating, preferably reducing or even eliminating, such microbial infections.

The presently useful antiseptic compositions may be in any suitable form, such as a cream, lotion, ointment, liquid and the like, and are preferably administered directly to the eye being cared for. Such administering can, and preferably does, include periodic or repeated applications of the chlorine dioxide-containing composition to the eye. Such periodic applications to eyes which are susceptible to, but do not have, microbial infections have been found to effectively prevent microbial infections from occurring in such eyes. In the event, as is preferred, the presently useful compositions are in the form of a liquid medium, the administering preferably comprises applying one or more drops of the liquid medium directly to the mammalian eye.

The amount of chlorine dioxide present in the presently useful antiseptic compositions is effective to act as an antiseptic in the eye. The amount of chlorine dioxide is preferably in the range of about 0.2 to about 15, more preferably about 0.5 to about 10 and still more preferably about 1 to about 5, ppm by weight of the composition. It has surprisingly been found that compositions which have such reduced concentrations of chlorine dioxide are very effective as antiseptics in the eye.

The presently useful antiseptic compositions preferably have a pH in the range of about 6 to about 10 and/or are substantially isotonic. Effective amounts of buffer components and/or tonicity adjusting components may be included to provide that such compositions have the desired pH values and/or tonicities. Buffer components and tonicity adjusting components useful in other ophthalmic-related compositions may be employed in the presently useful compositions. In addition, one or more other components, such as those known to be useful in ophthalmic-related compositions, may be included in the presently useful compositions in amounts effective to provide such compositions with one or more desired properties. For example, the form of the presently useful compositions may be obtained and/or maintained using one or more of such other components, as fillers, emollients, surfactants and the like.

Methods of irrigating ocular tissue during ophthalmic surgery are provided. In general, such irrigating methods comprise administering to an area of a mammalian eye undergoing a surgical procedure an amount of a composition effective to irrigate the area. Irrigation of an ocular area during ophthalmic surgery is often desirable, or even necessary, for example, to remove detached tissue, fluids and/or other debris from the area and/or to allow the surgeon to have an unobstructed view of the surgical area and/or to otherwise facilitate the surgical procedure. The presently useful irrigants may be employed to facilitate various ocular surgical procedures, for example, the removal and/or replacement of a natural lens in the eye, a vitrectomy, a corneal transplant and the like.

The presently useful ophthalmic surgical irrigant compositions are ophthalmically acceptable and include chlorine dioxide in an antimicrobially effective amount. Preferably, the above-noted administering step is effective in disinfecting the ocular surgical area, that is the area of the eye coming in contact with the irrigating composition. Thus, preferably the presently useful compositions include chlorine dioxide in an effective disinfecting amount. As used herein, a disinfecting amount of chlorine dioxide is such amount as to reduce the microbial burden or load by one log order in three hours or less, preferably in one hour or less, more preferably in ten minutes or less.

The presently useful irrigating compositions are preferably present in the form of a liquid medium, more preferably an aqueous liquid medium, and still more preferably have a pH in the range of about 6 to about 10 and/or are substantially isotonic. As described above with regard to the presently useful antiseptic compositions, buffer components and/or tonicity adjusting components and/or other components may be included in the presently useful irrigating compositions to provide such compositions have the desired pH values and/or tonicities and/or other beneficial properties.

Although any suitable concentration of chlorine dioxide may be included in the presently useful surgical irrigating compositions, it is preferred that the chlorine dioxide be present in an amount in the range of about 0.05 to about 10, more preferably about 0.1 to about 5 and still more preferably about 0.2 to 3, ppm by weight of the composition.

The presently useful chlorine dioxide-containing surgical irrigating compositions can be employed substantially as prior art ophthalmic surgical irrigants have been used. The presently useful chlorine dioxide compositions are effective ophthalmic surgical irrigants, are ophthalmically acceptable and, in addition, preferably are effective to disinfect the ocular surgical area with which the composition comes in contact.

The present methods preferably further comprise producing the chlorine dioxide-containing compositions from precursor compositions including chlorine dioxide precursor components. More preferably, this producing step occurs directly prior to the administering steps of the present methods. In this manner, the presently useful compositions can be produced when needed, and have a consistent and well controlled potency (effectiveness) or chemical make-up so as to be both effective as an ophthalmic antiseptic or an ophthalmic surgical irrigant and ophthalmically acceptable to avoid detrimentally affecting the eye being cared for or the ocular area undergoing surgery.

The media, preferably liquid media, useful in the present invention are selected to have no substantial detrimental effect on the eye or ocular tissue being cared for or irrigated and to allow and even facilitate the present eye care or ocular tissue irrigation. The media are preferably aqueous-based. A particularly useful aqueous liquid medium is that derived from saline, for example, a conventional saline solution or a conventional buffered saline solution. The aqueous media preferably have a pH in the range of about 6 to about 10, more preferably about 6 to about 8. The media preferably have ophthalmically acceptable tonicity levels, for example, of at least about 200 mOsmol/kg, more preferably in the range of about 200 to about 400 mOsmol/kg.

Included among the chlorine dioxide precursor components suitable for use are those which are adapted to provide for controlled formation of chlorine dioxide. Thus, such precursors allow chlorine dioxide to be shipped and stored with minimum loss of effectiveness. Chlorine dioxide is formed when needed and wanted, for example, in a liquid medium used in the present methods.

Specific examples of chlorine dioxide precursor components include metal chlorites, such as alkali metal and alkaline earth metal chlorites. Technical grade sodium chlorite is a very useful chlorine dioxide precursor component. Chlorine dioxide-containing complexes, such as complexes of chlorine dioxide with carbonate, chlorine dioxide with bicarbonate and mixtures thereof are also included as chlorine dioxide precursor components. The exact chemical composition of many chlorine dioxide precursor components, for example, stabilized chlorine dioxide (SCD) and the chlorine dioxide complexes, is not completely understood. The manufacture or production of certain chlorine dioxide precursor components is described in McNicholas U.S. Pat. No. 3,278,447, which is incorporated in its entirety herein by reference. Specific examples of useful SCD products include that sold under the trademark Dura Klor by Rio Linda Chemical Company, Inc., and that sold under the trademark Anthium Dioxide by International Dioxide, Inc. An especially useful SCD is a product sold under the trademark Purogene® by Bio-Cide International, Inc.

In general, the chlorine dioxide precursor component may be included in a medium, preferably a liquid medium, at a predetermined concentration, effective to produce the desired chlorine dioxide-containing composition.

In one embodiment, the chlorine dioxide precursor component includes a functionality selected from carbonate, borate, sulfate, phosphate, and mixtures thereof.

The chlorine dioxide precursor components useful in the present invention are those which form or produce chlorine dioxide in a liquid medium in response to at least one factor, preferably in the presence of an activator or promoter component. The presently useful compositions may further comprise an activator component in an amount effective to effect formation of chlorine dioxide, for example, an effective antiseptic amount or an effective antimicrobial amount of chlorine dioxide, from the chlorine dioxide precursor component.

Any suitable activator component may be employed to effect the generation of chlorine dioxide from the presently useful chlorine dioxide precursor components. Examples include, acidic materials to increase the acidity of the medium, transition metal components, oxygen-releasing components, organic acid anhydrides, chlorine dioxide reducing components and the like. In addition, an electrical current can be passed through a chlorine dioxide precursor-containing liquid medium to effect formation of chlorine dioxide.

Preferably, the composition used as an ophthalmic antiseptic or as an irrigant in ocular surgical procedures is substantially free of any activator (or other) component or residue thereof used to promote, e.g., activate, the production of chlorine dioxide from the chlorine dioxide precursor component. Thus, preferred activator components are those which effectively promote the production of chlorine dioxide without contaminating the final useful product. This feature reduces the risks that the useful product is irritating or otherwise harmful to the eye or ocular tissue being cared for or irrigated. Particularly useful activator components include such components which are present in a material phase, e.g., a solid phase, which is separate from the material phase, e.g., a liquid phase, containing the chlorine dioxide precursor component. In this manner, the activator component can be maintained separate from the resulting chlorine dioxide-containing composition. Very useful activator components include solid transition metal components.

At mildly acidic conditions, in particular at a pH of less than about 6 and especially in the range of about 3 to about 5, the production of chlorine dioxide is effected from the chlorine dioxide precursors. Any suitable acidic component may be employed as the activator component. The primary criteria for such acidic component is that it have the ability to increase the acidity of the liquid medium containing chlorine dioxide precursor sufficiently to effect formation of chlorine dioxide from such chlorine dioxide precursor, and preferably sufficiently to effect formation of antiseptic amounts or disinfecting amounts of chlorine dioxide from the presently useful chlorine dioxide precursors. Such acidic components should also have no substantial detrimental effect on the eye or ocular tissue being cared for or irrigated.

Examples of the presently useful acidic components include mineral acids, salts of such mineral acids, carboxylic acids, salts of such carboxylic acids and mixtures thereof. The mineral acids include, for example, citric acid, sulfuric acid, hydrogen halides, phosphoric acid and the like. The carboxylic acids include both mono- and poly-, e.g., di-, tri- and the like, carboxylic acids, and preferably include 1 to about 10 carbon atoms per molecule. One or more non-hydrocarbonaceous groups, e.g., hydroxy groups, halide groups and the like, may be appended to the carboxylic acid. If any acid salt is employed, it is preferred that the salt be an alkali or alkaline earth metal salt, more preferably an alkali metal salt. A particularly useful group of acidic components is selected from alkali metal hydrogen phosphates, citric acid, lactic acid, tartaric acid and mixtures thereof.

During chlorine dioxide generation using acid activation, it is preferred that the liquid aqueous medium have a pH of about 6 or less, in particular in the range of about 3 to about 5. The amount of acidic component employed is preferably sufficient to provide the precursor-containing liquid medium with the desired pH.

Any transition metal component capable of effecting the formation of chlorine dioxide from a chlorine dioxide precursor in an aqueous liquid medium, preferably at a pH between about 6 and about 10, or possibly higher, may be employed as the activator component. The primary criteria for such transition metal component is that it have the ability to effect formation of chlorine dioxide from a chlorine dioxide precursor. Such metal components should also have no substantial detrimental effect on the eye or ocular tissue being cared for or irrigated.

It is preferred that the activator component be present as a solid, for example, to avoid contaminating the final useful product with the activator or residue thereof. In certain embodiments, solid metals can be easily and conveniently introduced into or removed from the chlorine dioxide precursor-containing medium, as desired. The activator, for example, metal, component may be immobilized, or maintained substantially stationary, relative to the precursor-containing medium.

The particular metals of interest herein are the transition metals and mixture thereof, in particular from Group III metals, Group IV metals, Group V metals, Group VI metals, Group VII metals, Group VIII metals and mixture thereof.

Because of their high degree of effectiveness, platinum group metals and mixtures thereof, and especially platinum or palladium, are particularly useful. The platinum group metals include platinum, palladium, iridium, ruthenium, rhodium and osmium.

The metal component or components may be present in the metallic form and/or in a combined form as part of an organic or inorganic compound or complex.

The amount of metal component needed to practice this invention is to be viewed in terms of what quantity or surface area is useful to generate a particular concentration of chlorine dioxide in a given time and in light of the amount of precursor present in solution.

Oxygen-releasing components useful as activator components in the present invention include both inorganic and organic peroxy compounds.

In one embodiment, the oxygen-releasing components which may be used in the present invention are water soluble inorganic slats such as, for example, the sodium, potassium, calcium, magnesium, lithium and ammonium salts of oxygen-releasing sulfur compounds, such as, for example, the perthiosulfates ($S_2O_5^{-2}$), the persulfates ($SO_5^{-2}$), the peroxysulfates, such as the peroxymonosulfates ($HSO_5^{-1}$) and the peroxydisulfates ($S_2O_8^{-2}$), and mixtures thereof.

A particularly preferred oxygen-releasing component is potassium peroxymonosulfate ($KHSO_5$) and the preferred form of this component is the triple salt which is a combination of potassium peroxymonosulfate ($KHSO_5$), potassium hydrogen sulfate ($KHSO_4$) and potassium sulfate ($K_2SO_4$). This composition is an acidic, water soluble, oxygen releasing powder which is odorless, white, granular, stable and free flowing. Other alkali metal, e.g., sodium, and ammonium salts are also useful.

Among useful organic peroxy compounds are the aliphatic and aromatic percarboxylic acids based on the radical

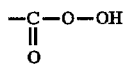

Organic peroxy compounds are preferably the aliphatic or aromatic percarboxylic acids and their alkali metal and ammonium salts. Examples of the aliphatic peracids include peracetic acid, perpropionic acid, up to perlauric acid. The preferred peracids are aromatic such as perbenzoic acid and nuclear substituted perbenzoic acids, especially those having melting points above 50° C. Especially preferred is p-methoxyperbenzoic acid.

The amount of oxygen-releasing component employed should be such as to be effective to effect formation of an effective amount of chlorine dioxide in the chlorine dioxide precursor-containing medium. The oxygen-releasing component is preferably present, for example, during the chlorine dioxide production, in an amount in the range of about 0.01 mole or less to about 1 mole or more per mole of potential chlorine dioxide present as chlorine dioxide precursor in the medium. Particularly useful results are achieved using oxygen releasing component in the range of about 0.01 mole to about 0.1 mole per mole of potential chlorine dioxide present as chlorine dioxide precursor in the medium.

In one embodiment, the activator component comprises an organic acid anhydride component in an amount sufficient to effect formation of chlorine dioxide from the precursor.

Any suitable organic acid anhydride component may be employed. The primary criteria for such component is that it have the ability to effect formation or generation of chlorine dioxide from the chlorine dioxide precursor component in the medium. Such organic acid anhydride components should also have no substantial detrimental effect on the eye or ocular tissue being cared for or irrigated.

Examples of useful organic acid anhydride components include succinic anhydride, glutaric anhydride, maleic anhydride and the like and mixtures thereof. The organic acid anhydride or anhydrides are preferably present during the chlorine dioxide producing step in an amount in the range of about 0.01 mole or less to about 1 mole or more per mole of potential chlorine dioxide present as chlorine dioxide precursor.

Any suitable chlorine dioxide reducing component may be used as an activator component in the present invention, provided that it functions as described herein and has no substantial detrimental effect, for example, on the eye or ocular tissue being cared for or irrigated. Examples of useful chlorine dioxide reducing components include, but are not limited to, sulfur-containing components, such as SH (group)—containing water soluble lower alcohols, dithiothreitol, bisulfites, thio urea, beta-mercaptoethanol, 2-mercaptopropionic acid, 2-mercapto-propionylglycine, 2-mercaptoethylaminehydrochloide, dithioerythritol, sulfites, pyrosulfites, thiosulfates, dithionites, glutathione and the like; N-acetylcysteine; acetylcysteine; cysteine hydrochloride ethyl ester; homocysteine; carbamoylcysteine; cysteine; cysteine hydrochloride; cysteinyl calycine; and the like and mixtures thereof. A particularly useful chlorine dioxide reducing component is selected from thiosulfates, for example, alkali metal thiosulfates and hydrogen thiosulfate and mixtures thereof.

The amount of chlorine dioxide reducing component employed should be such as to be effective to effect formation of chlorine dioxide, in a chlorine dioxide precursor-containing medium in which the chlorine dioxide reducing component is located. The chlorine dioxide reducing component is preferably present in an amount less than that amount effective to reduce all the potential chlorine dioxide formable from the chlorine dioxide precursor in the liquid medium. The chlorine dioxide reducing component may be present in an amount in the range of about 0.01 mole or less to about 0.5 mole or more per mole of potential chlorine dioxide present as chlorine dioxide precursor in the medium. Particularly useful results are achieved using amounts of chlorine dioxide reducing component in the range of about 0.01 mole to about 0.1 mole per mole of potential chlorine dioxide present as chlorine dioxide precursor in the medium.

The following non-limiting examples illustrate certain features of the present invention.

EXAMPLE 1

A conventional borate-buffered saline solution is selected. To this solution is added a stabilized chlorine dioxide product (a chlorine dioxide precursor), sold by Bio-Cide International Inc. under the trademark PUROGENE®. The amount of stabilized chlorine dioxide product added is sufficient to produce 5 ppm (by weight) of chlorine dioxide in the solution if all the stabilized chlorine dioxide product is converted to chlorine dioxide. The resulting solution has a pH of about 7.3, is substantially isotonic, and is ophthalmically acceptable.

A dispensing bottle is provided which includes a reservoir in which 50 ml of the above-noted solution is located. This bottle also includes an outlet tip through which the solution must pass when exiting the bottle. Located in this outlet tip are polyethylene beads on which palladium is deposited. The beads contain about 0.01% by weight palladium.

The palladium-containing polyethylene beads are present in an amount so that upon tipping the dispensing bottle upside down drops of the above-noted solution pass over the beads and exit the bottle. By passing over the beads, a portion of the stabilized chlorine dioxide product is converted to chlorine dioxide so that the solution exiting the bottle contains 2.5 ppm by weight of chlorine dioxide.

A human patient having bacterial conjunctivitis in both eyes uses the solution in the dispensing bottle as follows. Three times daily, the patient places three drops of the above-noted chlorine dioxide-containing solution directly from the dispensing bottle into each eye. The chlorine dioxide-containing solution has no detrimental effect on the eyes. In particular, no irritation or discomfort is apparent from using this solution. After a period of time, for example, in the range of about 3 to 5 days, the bacterial conjunctivitis is substantially alleviated as a result of placing the chlorine dioxide-containing solution in the eyes.

The above-noted procedure is continued until the bacterial infection is completely resolved.

EXAMPLE 2

A larger quantity of the above-noted stabilized chlorine dioxide product-containing borate buffered saline solution is prepared. This solution is sterilized.

A surgical procedure to remove the diseased natural lens from a human eye is conducted. As part of this surgical procedure, a liquid is used to irrigate the ocular tissue effected by the surgery, for example, to aid in the removal of the lens.

Approximately 1000 ml of the above-noted stabilized chlorine dioxide product-containing solution is passed over polyethylene beads on which palladium (0.01% by weight) is deposited. This causes a portion of the stabilized chlorine dioxide product to be converted to chlorine dioxide. A chlorine dioxide-containing solution containing 2.5 ppm by weight of chlorine dioxide is produced and is collected in a sterile container ready for use as a surgical irrigant. This chlorine dioxide-containing solution is used as an irrigant in the lens removal surgical procedure.

It is found that the solution is effective as a surgical irrigant. Further, the ocular tissue which comes in contact with this chlorine dioxide-containing irrigating solution is not detrimentally affected by this solution. In addition, because of the chlorine dioxide present in the solution, the ocular surgical area which comes in contact with the irrigant is effectively disinfected, thus reducing the risk of post-surgical infection.

While this invention has been described with respect to various specific examples and embodiments, it is to be understood that the invention is not limited thereto and that it can be variously practiced within the scope of the following claims.

What is claimed is:

1. A method of caring for a mammalian eye comprising:
   applying directly to a mammalian eye an effective, ophthalmically acceptable amount of a composition which includes chlorine dioxide in an amount effective as an antiseptic in said eye, said amount of chlorine dioxide being less than about 50 ppm by weight of said composition.

2. The method of claim 1 wherein said composition is in the form of an aqueous liquid medium.

3. The method of claim 2 wherein said composition has a pH in the range of about 6 to about 10.

4. The method of claim 3 wherein said composition is substantially isotonic.

5. The method of claim 1 which further comprises producing said composition from a precursor composition including a chlorine dioxide precursor component.

6. The method of claim 5 wherein said producing step occurs directly prior to said applying step.

7. The method of claim 5 wherein said composition is substantially free of any component or residue thereof used to promote the production of chlorine dioxide from said chlorine dioxide precursor component.

8. The method of claim 1 wherein said composition includes an amount of chlorine dioxide in the range of about 0.2 to about 15 ppm by weight.

9. The method of claim 1 wherein said composition includes an amount of chlorine dioxide in the range of about 0.5 to about 10 ppm by weight.

10. The method of claim 1 wherein said mammalian eye has a microbial infection and said applying is effective in treating said microbial infection.

11. The method of claim 1 wherein said applying comprises direct topical installation of said composition into said mammalian eye.

12. The method of claim 1 wherein said applying is repeated.

13. A method of irrigating ocular tissue during ophthalmic surgery comprising:
    administering directly to an area of a mammalian eye undergoing a surgical procedure an amount of a composition effective to irrigate said area, said composition being ophthalmically acceptable and including chlorine dioxide in an antimicrobially effective amount.

14. The method of claim 13 wherein said administering is effective in disinfecting said area.

15. The method of claim 13 wherein said composition is an aqueous liquid medium.

16. The method of claim 15 wherein said composition has a pH in the range of about 6 to about 10.

17. The method of claim 16 wherein said composition is substantially isotonic.

18. The method of claim 13 which further comprises producing said composition from a precursor composition including a chlorine dioxide precursor component.

19. The method of claim 18 wherein said producing step occurs directly prior to said applying step.

20. The method of claim 18 wherein said composition is substantially free of any component or residue thereof used to promote the production of chlorine dioxide from said chlorine dioxide precursor component.

21. The method of claim 13 wherein said composition includes an amount of chlorine dioxide in the range of about 0.05 to about 10 ppm by weight.

22. The method of claim 13 wherein said composition includes an amount of chlorine dioxide in the range of about 0.1 to about 5 ppm by weight.

* * * * *